United States Patent [19]

Behrmann et al.

[11] Patent Number: 5,973,012
[45] Date of Patent: Oct. 26, 1999

[54] HYDROCARBON SYNTHESIS CATALYST SLURRY REJUVENATION WITH GAS DISENGAGEMENT (LAW 783)

[75] Inventors: William C. Behrmann; Stephen C. Leviness, both of Baton Rouge, La.

[73] Assignee: Exxon Research and Engineering Co., Florham Park, N.J.

[21] Appl. No.: 09/182,902

[22] Filed: Oct. 30, 1998

[51] Int. Cl.$^6$ .................................................. C07C 27/00
[52] U.S. Cl. .............................. 518/700; 502/21; 502/22; 502/53; 422/219
[58] Field of Search ................................ 518/700; 502/21, 502/22, 53; 585/899, 922; 422/219

[56] References Cited

U.S. PATENT DOCUMENTS 5,268,344 12/1993 Pedrick et al. ............................ 502/30
5,382,748 1/1995 Behrmann et al. ..................... 585/899

*Primary Examiner*—Shailendra Kumar
*Assistant Examiner*—Sreeni Padmanabhan

[57] ABSTRACT

A reversibly deactivated, particulate catalyst in a slurry hydrocarbon synthesis slurry is rejuvenated by circulating the slurry from a slurry body through (i) a gas disengaging zone to remove gas bubbles from the slurry, (ii) a catalyst rejuvenation zone in which a catalyst rejuvenating gas contacts the catalyst in the slurry to rejuvenate it and form a rejuvenated catalyst slurry and, (iii) back into the slurry body. Removing at least a portion of the gas bubbles improves the rejuvenation process.

12 Claims, 2 Drawing Sheets

HYDROCARBON SYNTHESIS CATALYST SLURRY REJUVENATION WITH GAS DISENGAGEMENT (LAW 783)

BACKGROUND OF THE DISCLOSURE

1. Field of the Invention

The invention relates to a process and apparatus for in-situ rejuvenating solid catalyst particles suspended in a slurry. More particularly, the invention relates to a process and means for rejuvenating solid catalyst particles dispersed in a three phase, Fischer-Tropsch type hydrocarbon slurry comprising said particles, a hydrocarbon liquid phase and gas bubbles in-situ in the slurry, in which gas bubbles are removed from the slurry entering the rejuvenation zone.

2. Background of the Invention

Slurry hydrocarbon synthesis (HCS) processes are known. In a slurry HCS process a synthesis gas (syngas) comprising a mixture of $H_2$ and CO is bubbled up as a third phase through a slurry in a reactor in which the slurry liquid comprises hydrocarbon products of the synthesis reaction and the dispersed, suspended solids comprise a suitable Fischer-Tropsch type hydrocarbon synthesis catalyst. Reactors which contain such a three phase slurry are sometimes referred to as "bubble columns", as is disclosed in U.S. Pat. No. 5,348,982. Irrespective of whether the slurry reactor is operated as a dispersed or slumped bed, the mixing conditions in the slurry will typically be somewhere between the two theoretical conditions of plug flow and back mixed. Syngas made from hydrocarbon feedstocks which contain nitrogen (i.e., natural gas) or nitrogen containing compounds (i.e., resids, coal, shale, coke, tar sands, etc.) invariably contains HCN and $NH_3$ which contaminate the reactive slurry and rapidly, but reversibly, deactivate the catalyst. Certain oxygenates and carbonaceous compounds formed in the slurry as by-products of the HCS reaction can also cause rapid deactivation. Deactivation of such catalysts by these species is reversible and catalytic activity is restored (the catalyst rejuvenated) by contacting the deactivated catalyst with hydrogen. The activity of the HCS catalyst in the reactive slurry may be intermittently or continuously rejuvenated by contacting the slurry with hydrogen or a hydrogen containing gas to form a rejuvenated catalyst slurry as is disclosed, for example, in U.S. Pat. Nos. 5,260,239 and 5,268,344. In these patents the slurry, containing gas bubbles, is rejuvenated by circulating it through either a rejuvenation tube immersed in the slurry or in an external rejuvenation reactor. It has now been found that the presence of CO hinders catalyst rejuvenation until the CO is consumed. This limits the overall efficiency of the rejuvenation process and wastes CO and $H_2$. It would be an improvement to the art if these gas bubbles could be removed from the slurry before it contacts the rejuvenation gas.

SUMMARY OF THE INVENTION

The present invention relates to a process and means for rejuvenating solid catalyst particles in a three phase hydrocarbon synthesis (HCS) slurry which comprises gas bubbles and catalyst particles dispersed in a slurry liquid, in which gas bubbles are removed from the slurry prior to the rejuvenation. Briefly, the process comprises passing a portion of slurry from a slurry body through a gas disengaging zone to remove gas bubbles and then through a catalyst rejuvenating zone in which the gas reduced slurry contacts a rejuvenation gas to rejuvenate the catalyst in the slurry. The rejuvenated slurry is then returned to the slurry body. This may be accomplished using a hollow rejuvenation tube, open at the top and bottom and immersed in the slurry, the bottom of which opens into an upwardly open gas disengaging cup surrounding the bottom of the tube, to provide an annular gas disengaging zone. The catalyst rejuvenation is done either continuously or intermittently, as desired, with the slurry reactor either operating and producing hydrocarbon products, or with it off-line. The gas bubbles comprise unreacted synthesis gas (syngas) and gas products of the HCS reaction. The slurry liquid comprises hydrocarbon products of the HCS reaction which are liquid at the reaction conditions. Thus, the process of the invention comprises rejuvenating a particulate, reversibly deactivated HCS catalyst in a slurry comprising gas bubbles, the catalyst and a slurry liquid in which at least a portion of the catalyst particles are at least partially, reversibly deactivated, by withdrawing a portion of slurry from a slurry body and passing or circulating it through a gas disengaging zone to disengage and remove gas bubbles from the slurry to form a gas reduced slurry, passing the gas reduced slurry through a rejuvenation zone in which it contacts a catalyst rejuvenating gas to rejuvenate the catalyst and form a rejuvenated catalyst slurry, followed by returning the rejuvenated slurry back into the slurry body. In the embodiment in which the rejuvenation zone is a hollow conduit oriented primarily vertically, the rejuvenating gas is injected into the bottom of the rejuvenating zone and the process continues as long as the rejuvenation gas, which also acts as a lift gas for the slurry in the rejuvenation zone, continues to be injected into the rejuvenation zone. In a slurry HCS reactor, synthesis gas comprising a mixture of $H_2$ and CO is bubbled up into the bottom of the reactor and forms gas bubbles which are dispersed in the slurry liquid. The presence of CO in the rejuvenation zone hinders catalyst rejuvenation until the CO is consumed. Further, the $H_2$ to CO ratio in the rejuvenation zone is substantially greater than the stoichiometric 2.1/1 and may be higher than 10/1. This means that instead of being converted to more desirable liquid hydrocarbon products, the CO in the rejuvenation zone is converted primarily to methane, thereby wasting valuable syngas and added hydrogen. The gas bubbles also contain gas reaction products of the HCS reaction, of which 50% or more may be water vapor, which interferes with the catalyst rejuvenation by acting as a diluent for the rejuvenation gas. The catalyst rejuvenation is accomplished within the slurry either in the HCS reactor or reaction zone, or in an outboard or separate catalyst rejuvenation zone or reactor, as is disclosed in U.S. Pat. No. 5,260,239. However, it is convenient to rejuvenate the catalyst within the slurry in the HCS reaction zone. When performed in the slurry in the HCS reactor, the HCS reaction is not disturbed as the gas disengaging and catalyst rejuvenation zones, while immersed in the slurry, are separate from it and the rejuvenation occurs within a rejuvenation conduit or tube in the slurry. While the practice of the invention finds particular use with rejuvenating an HCS catalyst in-situ in a hydrocarbon slurry liquid, it is not intended to be limited to this particular embodiment. By reversibly deactivated catalyst is meant that the catalyst is at least partially reversibly deactivated and that the catalytic activity is at least partially restored by contacting the catalyst in the slurry with a suitable catalyst rejuvenating gas. By immersed in the slurry is meant that at least the gas disengaging zone and the bottom portion of the rejuvenation zone are immersed in the slurry body. The top of the rejuvenation zone may be out of the slurry body. The slurry body may be a reactive slurry in a slurry reaction zone, such as a three phase slurry comprising a hydrocarbon liquid in which is dispersed catalyst particles and reactive gas bubbles, as in a slurry type HCS reaction zone disclosed in the prior art, or it may be separate from a reaction zone as disclosed in the '239 patent referred to above. The term "slurry body" is used herein to refer to the slurry body from which a portion is withdrawn and passed into the rejuvenation zone or the slurry body into which the rejuvenated slurry is passed into (they may both be the same body), to distinguish it from the slurry in the rejuvenation zone and the regenerated slurry exiting the rejuvenation zone. While the catalyst rejuvenation zone is separate from the slurry body, in some embodiments all or at least a portion of it may be located within the slurry body. In the context of the invention, the term "catalyst deactivating species" is meant to include species which reversibly deactivate the catalyst and wherein the catalyst activity is restored (the catalyst rejuvenated) by contact with a rejuvenating gas in-situ in the slurry liquid. Hydrogen or a hydrogen containing gas is useful for such rejuvenation, as has been demonstrated in the prior art. Finally, while HCN, $NH_3$ and certain types of oxygenates and carbonaceous materials will deactivate the catalyst, the invention is not intended to be limited to use only with these species, but is usefull with any species which reversibly deactivate the catalyst and wherein the catalyst activity can be restored with an appropriate rejuvenating gas.

DETAILED DESCRIPTION

Figure 1A:
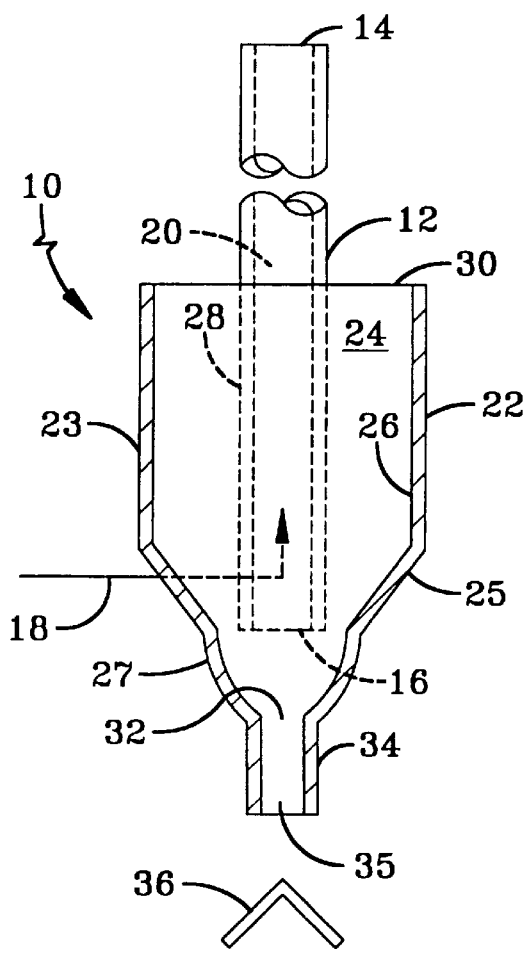
FIGS. 1(a) and 1(b) are a respective simplified schematic in partial crosssection and a top plan view illustrating a slurry gas disengaging and catalyst rejuvenating means useful in the practice of the invention.

In one embodiment the slurry degassing and catalyst rejuvenating means comprises a substantially vertical, hollow conduit open at the top and bottom and having means for injecting a catalyst rejuvenating gas into its interior, the bottom of which opens into a generally cup-shaped baffle which surrounds the bottom of the conduit and opens upward to provide an annular gas disengaging zone around the bottom of the conduit. Slurry containing deactivated catalyst flows down through the gas disengaging zone to disengage the gas and form a gas reduced slurry which passes up into the catalyst rejuvenating zone in which it is contacted and mixed with the upflowing catalyst rejuvenating gas which contacts the deactivated catalyst in the slurry, thereby at least partially rejuvenating the catalyst in the slurry to form a rejuvenated catalyst slurry. The rejuvenated catalyst slurry passes up and out the top of the rejuvenation zone and back into the slurry body. The terms "rejuvenating" and "rejuvenation" are used synonymously herein. The uprising rejuvenating gas is fed into the bottom of the rejuvenation conduit and acts as a lift gas to provide a net upward flow of the slurry through the conduit. This sets up a continuous flow of slurry through the gas disengaging and catalyst rejuvenating zones. This process continues as long as rejuvenating gas is fed into the rejuvenating conduit. Thus, the practice of the invention rejuvenates the catalyst in the slurry in the slurry reactor itself, without the need for an outboard rejuvenating reactor as in U.S. Pat. No. 5,260,239 and without interfering with the HCS reaction. The means employed to accomplish this is extremely simple, inexpensive, robust, has no moving parts, occupies a minimum of space in the reactor and also aids in dispersing the catalyst in the reactor and reducing catalyst maldistribution, because the slurry is preferably withdrawn near the bottom of the reactor where the catalyst concentration is greatest and returned at the top of the slurry where it is least. In a further embodiment, the gas disengaging and catalyst rejuvenating means form a single unit which terminates near the bottom of the slurry body, in which the gas disengaging means is a simple cup-shaped device, the wall of which surrounds the bottom of the conduit and is laterally spaced apart from the outer conduit surface, to form an annular flow path for the slurry to flow through and disengage gas, before entering the rejuvenating means, which may simply be a metal tube or pipe into which a catalyst rejuvenating gas is injected at a point or points, and preferably into the bottom portion in order to be most efficient. In a still further embodiment, the bottom of the gas disengaging means will have an orifice open to the main reactor slurry below, to prevent the build-up of catalyst particles and plugging of the unit. Still further, a simple baffle below the bottom orifice prevents feed gas from entering into the rejuvenation zone, while presenting no impediment to the downward flow of catalyst particles out the bottom of the cup.

Figure 1B:
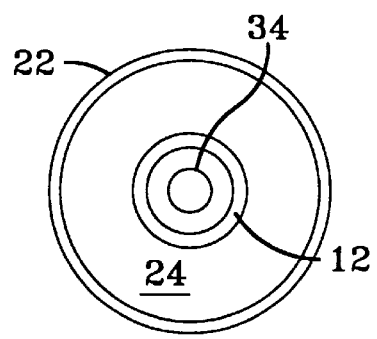
Figure 2:
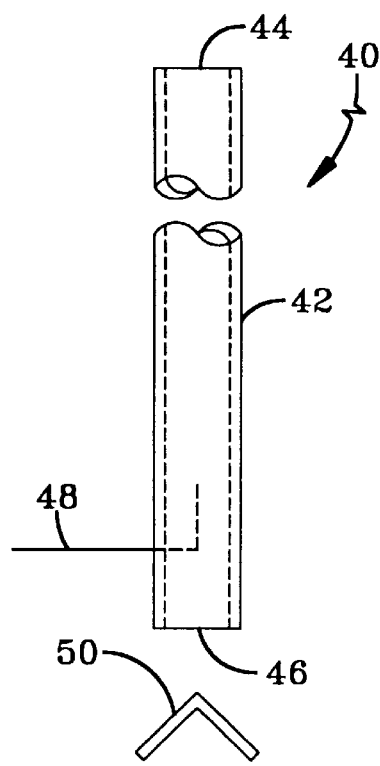
FIG. 2 is a simple schematic of a prior art rejuvenation tube.

Referring to FIGS. 1(a) and 1(b) there is schematically illustrated a simplified, partial cross section of a slurry gas disengaging and catalyst rejuvenating means 10 useful in the practice of the invention which comprises a hollow, vertical conduit or pipe 12 open at its top 14 and bottom 16 with means 18 for injecting catalyst rejuvenating gas into the bottom of the conduit, which means is a simple gas line with a nozzle (not shown) at the end inside the catalyst rejuvenating zone 20 which is the interior of the conduit. Conduit 12 is simply a metal pipe in the embodiment shown. A hollow metal cup 22 of cylindrical cross section surrounds the bottom of the conduit to form an annular space 24 between the inner surface 26 of the cup and the outer surface 28 of the conduit, with the cup extending down past the bottom 16 of the conduit to form an open space 32 just below the open bottom of the conduit. The catalyst rejuvenation means 10 is that illustrated in FIGS. 1(a) and 1(b). The top 30 of the cup is open and the bottom contains an orifice, which in this embodiment is illustrated as a nozzle 34, to permit catalyst particles which may have disengaged from the slurry flowing down through the annular space 24 and up into the catalyst rejuvenating zone 20 to exit the bottom of the cup through nozzle 34, where they return to the slurry. This prevents catalyst particles from collecting in the bottom of the cup and possibly plugging it and preventing or reducing slurry flow up into the catalyst rejuvenation zone. In the embodiment shown, the cup 22 has a vertical, cylindrical side wall 23 which successively terminates at its bottom in a cone shaped section 25, a curved section 27 and finally nozzle 34. Curved section 27 provides more space for slurry flow than a continuation of the conical section would and also provides a space for any disengaged catalyst particles to fall to the bottom of the cup and down through the nozzle back into the slurry. A simple metal baffle 36 placed below the exit 35 of nozzle 34 prevents the CO containing synthesis gas bubbling up through the reactor from entering into the cup and rejuvenation zone, without impeding the downflow and exit through nozzle 34 of disengaged catalyst particles. In contrast to the invention, FIG. 2 is a simple schematic of a rejuvenation tube 40 of the prior art which simply comprises a vertically disposed metal tube 42, open at its top 44 and bottom 46. A gas line 48 injects catalyst rejuvenating gas into the tube to rejuvenate the reversibly deactivated catalyst in the slurry flowing up through the tube by virtue of the lifting action of the rejuvenating gas. As long as the rejuvenating gas is flowing up through the tube, a constant flow of gas reduced slurry containing reversibly deactivated catalyst particles flows up through the tube in which the gas contacts the catalyst particles and rejuvenates them, while the catalyst rejuvenated slurry exits out the top back into the slurry body in (not shown) in which the tube is totally immersed. A simple cone shaped baffle 50, prevents syngas bubbles from entering up into the rejuvenating tube and impairing or preventing catalyst rejuvenation.

Figure 3:
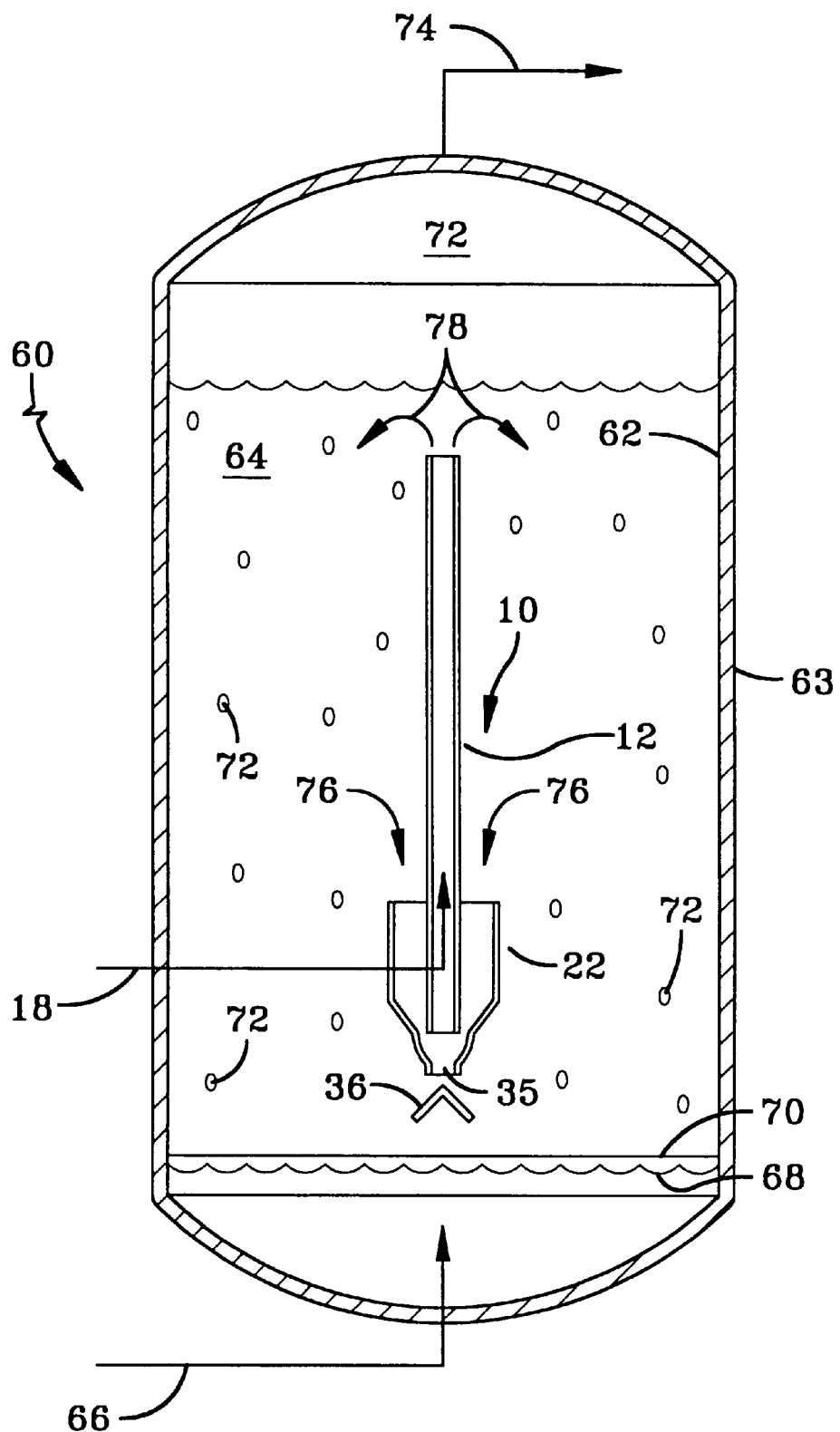
FIG. 3 schematically illustrates a slurry reactor containing a slurry in which is immersed a slurry gas disengaging and catalyst rejuvenating means of the invention.

FIG. 3 is a simple schematic of an HCS slurry reactor 60 which comprises a steel cylindrical vessel 62 containing a three phase, reactive HCS slurry 64 within, in which a gas disengaging and catalyst rejuvenating means 10 of the invention is shown as being totally immersed in the slurry. The syngas is introduced into the bottom of the reactor via gas line 66 and is bubbled up into the slurry by suitable gas distribution means (not shown) horizontally arranged across the surface of gas and liquid impermeable plate 70, which is sealed to the interior of the vertical wall 63 of vessel 62. Bubbles 72 of unreacted syngas and gas products of the HCS reaction rise up through and out of the slurry into gas disengaging and collecting zone 72 and are removed from the reactor via line 74. Not shown is filtration means, such as one or more liquid filters in the reactive slurry 64 or in one or more filtration vessels external of the reactor. Such filtration means separate the hydrocarbon slurry liquid from the catalyst particles as filtrate, and pass the filtrate to further processing and upgrading. Magnetic means may also be used to separate the catalyst particles from the hydrocarbon liquid product if the catalyst particles are magnetic or paramagnetic, as is disclosed in the prior art. As shown in FIG. 1, the gas disengaging and catalyst rejuvenating means of the invention 10 comprises a vertical, hollow tube or pipe 12, open at its top and bottom, with the gas disengaging cup 22 surrounding the bottom of the tube. The interior of the tube 12 is the catalyst rejuvenating zone and is provided with rejuvenating gas injecting means 18 for injecting catalyst rejuvenating gas into the interior of the tube near the bottom thereof. A simple cone shaped baffle plate 36 is disposed below the opening or orifice 35 at the bottom of the cup 22 to prevent the uprising reactive gas from entering into either the annular gas disengaging space 24 or the rejuvenating zone 20. Arrows 76 indicate the downward flow of the slurry containing the reversibly deactivated catalyst particles into the gas disengaging zone 24 and arrows 78 indicate the outward flow and return of the catalyst rejuvenated slurry back into the slurry in the reaction zone (the slurry body) out the top of the rejuvenation conduit 12.

The uprising syngas serves to maintain the catalyst particles in suspension in the hydrocarbon slurry liquid. As soon as slurry enters a relatively quiescent zone in which the uprising gas bubbles do not enter, the lighter gas bubbles immediately begin disengaging from the slurry liquid. At the same time, the heavier catalyst particles begin to settle out due to gravity and the lack of the uplifting effect of the reactive gas bubbles. Thus, the annular zone 24 between the inner wall surface of the cup 22 and the outer wall surface of the rejuvenation tube 12 provides a quiescent zone for the slurry passing down through the zone. The outer wall of the cup and the baffle prevent uprising gas from entering the quiescent zone and gas bubbles immediately begin disengaging from the slurry as soon as it enters the zone. The volumetric size of the zone, its length, slurry flow rate and gas disengaging rate are factored to size the zone so as to effectively remove most of the gas bubbles before the slurry enters up into the bottom 16 of the rejuvenation tube. The slurry flow rate through the tube is determined in large measure by the tube diameter and rejuvenation gas flow rate. Bubble rise velocity is a strong function of the bubble size and the gas disengaging cup is sized so that the downward velocity of the slurry (total flow divided by the disengaging means cross sectional area) is less than the rise velocity of the smallest bubbles it is desired to remove. Studies have shown that as much or more than 90% of the gas bubbles may be removed from the slurry in this manner, before it goes into the rejuvenation tube. The catalyst settling rate must also be taken into account to prevent the catalyst particles from plugging or slowing the flow of slurry into the rejuvenating zone. Thus, while an orifice or nozzle at the bottom of the cup or disengaging zone may not always be necessary, it serves as insurance in the event of an imbalance in the slurry reactor, such as a slumped bed catalyst condition in which the catalyst concentration toward the bottom of the slurry is temporarily greater than what the disengaging and rejuvenating means was designed for, which could cause catalyst accumulation at the bottom of the cup. The gas disengaging means and the catalyst rejuvenating means have been illustrated as having a cylindrical cross section, but other shapes such as rectilinear and polygonal could be used if desired. While the rejuvenation tube is shown as vertical and wholly immersed in the slurry, some departures from vertical may be used and the tube or conduit may be bent to accommodate other mechanical devices in the reactor. However, vertical orientation is preferred. In one embodiment, which is a preferred embodiment, the top of the rejuvenation zone or conduit may extend up out of the top of the slurry and/or feed the catalyst rejuvenated slurry to gas separating means (not shown) for separating and removing offgas formed by the catalyst rejuvenation from the rejuvenated catalyst slurry. The slurry from which the offgas has been removed is then passed back into the slurry body or elsewhere. Another aspect of the present invention is that of concentrating the catalyst in the slurry in the gas disengaging zone, which occurs by virtue of releasing the gas bubbles to form a denser slurry in which the catalyst is more concentrated. The hydrogen or hydrogen containing catalyst rejuvenation gas injected into the rejuvenation zone comprises hydrogen which may contain other gasses such as nitrogen, $CO_2$, $H_2O$, $CH_4$, $C_2-C_{4+}$ hydrocarbons, and also CO (as long as the mole ratio of the $H_2$ to CO) is sufficient to remove the CO and still at least partially rejuvenate the catalyst.

As disclosed in U.S. Pat. No. 5,288,673, the degree of catalyst rejuvenation can be controlled by independently controlling the slurry temperature in the rejuvenating zone irrespective of the temperature of the main body of slurry in the surrounding HCS reaction zone. This patent discloses that temperature control in the rejuvenation zone or tubes is achieved by one or more of either increasing or decreasing the slurry residence time in the zone, so as to utilize the exothermic nature of the rejuvenation reactions, by insulating the rejuvenation tubes, by introducing heat or a cooling medium into the zone, by preheating the rejuvenation gas, etc. The '673 patent teaches that the temperature in the rejuvenation zone should be high enough to remove CO and at least partially rejuvenate the catalyst and low enough to minimize methane formation and wax ($\sim C_{20+}$ alkanes) hydrogenolysis. These teachings apply to the present invention also.

In an HCS process, liquid and gaseous hydrocarbon products are formed by contacting a syngas comprising a mixture of $H_2$ and CO with a suitable Fischer-Tropsch type of HCS catalyst, under shifting or non-shifting conditions and preferably non-shifting conditions in which little or no water gas shift reaction occurs, particularly when the catalytic metal comprises Co, Ru or mixture thereof. Suitable Fischer-Tropsch reaction types of catalysts comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg, La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A slurry hydrocarbon synthesis process comprising passing a synthesis gas comprising a mixture of hydrogen and carbon monoxide into a slurry body comprising said slurry which comprises gas bubbles and a particulate hydrocarbon synthesis catalyst in a hydrocarbon slurry liquid, in which said hydrogen and carbon monoxide react at hydrocarbon synthesis conditions, in the presence of said catalyst to produce liquid and gaseous hydrocarbon synthesis products, including $C_{5+}$ hydrocarbons, wherein said synthesis reaction reversibly deactivates said catalyst particles and wherein said slurry liquid comprises hydrocarbon products which are liquid at said synthesis conditions, said process further comprising rejuvenating said reversibly catalyst particles in-situ in said slurry by (i) passing a portion of said slurry containing said reversibly deactivated catalyst particles from said slurry body down through an upward opening, hollow gas disengaging zone immersed in said body, peripherally surrounding and located proximate the bottom or slurry entrance of a catalyst rejuvenation means which comprises a substantially vertical, hollow conduit open at the top and bottom and immersed in said slurry, the interior of which comprises a catalyst rejuvenation zone and with said open bottom and top respectively comprising a slurry entrance and exit, to disengage and remove at least a portion of said gas bubbles from said slurry to form a gas reduced slurry, (ii) passing said gas reduced slurry and a catalyst rejuvenating gas comprising up into and through said rejuvenation zone in which said hydrogen rejuvenates said catalyst and forms a rejuvenated catalyst slurry which passes out of the top of said rejuvenating zone, followed by (iii) passing said rejuvenated slurry back into said slurry body.

2. A process according to claim 1 wherein said catalyst rejuvenation gas also acts as a lift gas in said zone to enable said slurry to pass into up into and out of the top of said catalyst rejuvenation means.

3. A process according to claim 1 wherein at least a portion of said hydrocarbon synthesis product is sent to further processing which comprises one or more of (i) fractionation and (ii) at least one conversion operation, in which at least a portion of its molecular structure is changed.

4. A process according to claim 3 wherein said gas disengaging zone comprises a hollow, upward opening and cup-shaped body surrounding said bottom of said rejuvenation conduit in said slurry, to provide an annular flow path for said slurry between the interior of said means and the exterior of said conduit.

5. A process according to claim 4 wherein said conduit slurry exit is not immersed in said slurry body.

6. A process according to claim 4 wherein said conversion comprises at least one hydroconversion operation.

7. A process according to claim 6 wherein said hydroconversion comprises catalytic hydroconversion.

8. A slurry hydrocarbon process wherein a synthesis gas comprising a mixture of hydrogen and carbon monoxide is passed up into a three phase slurry body comprising gas bubbles and a particulate hydrocarbon synthesis catalyst in a hydrocarbon synthesis reactor at synthesis reaction conditions effective for said hydrogen and carbon monoxide to react and form hydrocarbon products which are withdrawn from said reactor, at least a portion of which are liquid at said synthesis conditions and comprise said slurry liquid, wherein said synthesis reaction reversibly deactivates said catalyst, and wherein said catalyst can be rejuvenated by contact with hydrogen, also comprises rejuvenating said reversibly deactivated catalyst particles by circulating slurry containing said deactivated catalyst particles from said slurry body up into a catalyst rejuvenation zone comprising the interior of a substantially vertically oriented, hollow conduit open proximate its top and bottom, at least the bottom portion of which is immersed in said slurry body and opens into a slurry gas disengaging means, wherein slurry is passed from said body into said gas disengaging means to remove at least a portion of said gas bubbles which contain unreacted CO and also water vapor and form a gas reduced slurry which is passed up into said conduit in which it contacts a hydrogen-containing rejuvenation gas passed into said conduit to at least partially restore the activity of said catalyst and form a rejuvenated catalyst slurry which passes up and out of the top of said conduit and back into said slurry body.

9. A process according to claim 8 wherein the mole ratio of said rejuvenating hydrogen to unreacted CO in said rejuvenation zone is greater than 2.1/1.

10. A process according to claim 9 wherein said withdrawn product is upgraded by one or more of (i) fractionation and (ii) a conversion operation in which at least a molecular structure of said hydrocarbon is changed.

11. A process according to claim 10 wherein said conversion comprises hydroconversion.

12. A process according to claim 11 wherein said hydroconversion comprises catalytic hydroconversion.

* * * * *